(12) United States Patent
Phelps et al.

(10) Patent No.: US 7,060,473 B2
(45) Date of Patent: Jun. 13, 2006

(54) FERMENTATIVE PROCESS FOR MAKING INORGANIC NANOPARTICLES

(75) Inventors: Tommy J. Phelps, Knoxville, TN (US); Robert J. Lauf, Oak Ridge, TN (US); Ji-Won Moon, Oak Ridge, TN (US); Yul Roh, Gwangju (KR)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 11/227,586

(22) Filed: Sep. 15, 2005

(65) Prior Publication Data

US 2006/0014261 A1    Jan. 19, 2006

Related U.S. Application Data

(63) Continuation-in-part of application No. 10/174,184, filed on Jun. 18, 2002, which is a continuation-in-part of application No. 09/428,376, filed on Oct. 28, 1999, now Pat. No. 6,444,453.

(51) Int. Cl.
*C12P 3/00* (2006.01)
*C01B 13/00* (2006.01)
*C01G 57/00* (2006.01)

(52) U.S. Cl. .................... 435/168; 423/593.1; 977/898

(58) Field of Classification Search ................ 435/168; 423/593.1; 977/898
See application file for complete search history.

(56) References Cited

U.S. PATENT DOCUMENTS 6,444,453 B1    9/2002    Lauf et al.

FOREIGN PATENT DOCUMENTS

WO    WO 2005/073407    8/2005

OTHER PUBLICATIONS

Dunin-Borkowski et al., "Magnetic Microstructure of Magnetotactic Bacteria by Electron Holography," Science, 1998, pp. 1868-1870, vol. 282.

Liu et al., "Thermophilic FE(III)-Reducing Bacteria from the Deep Subsurface: The Evolutionary Implications," Science, 1997, pp. 1106-1109, vol. 277.

Lovely, "Dissimilatory Metal Reduction," Annu Rev Microbiol, 1993, pp. 263-290, vol. 47.

Lovely et al., "Anaerobic Production of Magnetite by a Dissimilatory Iron-Reducing Microorganism," Nature, 1987, pp. 252-254, vol. 330.

Nealson and Saffarini, "Iron and Manganese in Anaerobic Respiration: Environmental Significance, Physiology, and Regulation," Annual Rev. Microbiol, 1994, pp. 311-343, vol. 48.

Rickard, "The Microbiological Formation of Iron Sulfides," Stockholm Contrib Geol, 1969, pp. 49-66, vol. 20.

Perry et al., "Geology and Stable Isotope Geochemistry of the Biwabik Iron Formation, Northern Minnesota," Econom Geol, 1973, pp. 1110-1125, vol. 68.

Zhang et al., "Enhancement of Fe(III), Co(III) and Cr(VI) Reduction at Elevated Temperatures & by a Thermophilic Bac.," Appl Biochem and Biotech, 1996, pp. 923-932, vol. 57-58.

Zhang et al., "Physiochemical, Mineralogical, and Isotopic Characterization of Magnetite-Rich . . . ," Geochimica et Cosmochimica Acta, 1997, pp. 4621-4632, vol. 61, No. 21.

Zhang et al., "Iron Reduction by Psychrotropic Enrichment Cultures," FEMS Microbiology Ecology, 1999, pp. 367-371, vol. 30.

Zhang et al., "Formation of Single-Domain Magnetite by a Thermophilic Bacterium," American Mineralogist, 1998, pp. 1409-1418, vol. 83.

*Primary Examiner*—Herbert J. Lilling
(74) *Attorney, Agent, or Firm*—Joseph A. Marasco

(57) ABSTRACT

A method for producing mixed metal oxide compounds includes the steps of: providing a supply of a metal reducing bacteria; providing a culture medium suitable for growth of the bacteria; providing a first mixed metal oxide phase comprising at least a first and a second metal, at least one of the first and second metal being reducible from a higher to a lower oxidation state by the bacteria; and, combining the bacteria, the culture medium, the first mixed metal oxide, and at least one electron donor in a reactor, wherein the bacteria reduces at least one of the first metal and the second metal from the higher to the lower oxidation state to form a second mixed metal oxide phase.

18 Claims, 4 Drawing Sheets

FERMENTATIVE PROCESS FOR MAKING INORGANIC NANOPARTICLES

CROSS-REFERENCE TO RELATED APPLICATIONS

This application is a Continuation-In-Part of application Ser. No. 10/174,184 entitled MIXED OXIDE NANOPARTICLES AND APPARATUS FOR MAKING SAME, filed on Jun. 18, 2002, which was a Continuation-In-Part of application Ser. No. 09/428,376 filed on Oct. 28, 1999, now U.S. Pat. No. 6,444,453, issued on Sep. 3, 2002 entitled MIXED OXIDE NANOPARTICLES AND METHOD FOR MAKING, the entire disclosures of which are incorporated herein by reference.

The United States Government has rights in this invention pursuant to contract no. DE-AC05-00OR22725 between the United States Department of Energy and UT-Battelle, LLC.

FIELD OF THE INVENTION

The present invention relates to the field of inorganic synthesis, and more particularly, to methods of making fine particulates of ceramic powders using anaerobic bacteria to reduce a starting mixed oxide composition from a higher to a lower oxidation state.

BACKGROUND OF THE INVENTION

It has been known for some time that certain bacteria reduce Fe(III) in various geochemical environments. Microbial Fe(III) reduction has been observed primarily in low temperature environments that have been extensively influenced by modern surface biogeochemical processes such as weathering or microbial metabolism. It is also known that certain bacteria such as *Desulfovibrio desulfuricans* reduce sulfate to sulfide under anaerobic conditions. The formation of some mineral deposits such as magnetite deposits in banded iron formations in both ancient and modern times may be attributed to the action of such bacteria.

Some magnetotactic bacteria have been reported to form magnetic nanocrystals within the cell. However, the reported ratio of product nanocrystals to biomass is relatively low, typically a few nanocrystals per cell.

Several varieties of thermophilic bacteria such as *Thermoanerobacter* and *Thermoanerobium* are known to reduce Fe(III) ions as part of their respiration processes. Applicants' co-pending U.S. patent application Ser. No. 10/174,184 discloses the use of these microorganisms to create novel mixed metal oxide compositions in which at least one of the metals is reducible by the bacteria and in which other metal(s) may or may not be reducible by the bacteria.

In U.S. Pat. No. 6,444,453 methods are taught for using bacterial reduction to make doped or mixed metal oxides, particularly ferrites. A suspension of amorphous Fe(III) oxyhydroxide is used as the source of iron and the dopants are added as various soluble species in the culture medium. Specifically, Zn is added as $ZnCl_2$, Co added as $CoCl_2$ or as Co(III)-EDTA, and Cr is added as $K_2CrO_4$. Those skilled in the art will appreciate that the method taught in '453 will be limited in some cases by the potential toxicity of these soluble species to the bacteria. Toxicity may preclude the use of some dopants completely and in other cases may limit the overall productivity by limiting the usable concentration of a particular dopant in solution to some maximum that is tolerable by the bacteria.

OBJECTS OF THE INVENTION

Accordingly, objects of the present invention include the following: providing a method for making mixed metal oxide nanoparticles using bacterial reduction of higher oxides; providing a method for incorporating dopant species into mixed metal oxide nanoparticles; increasing the amount of dopants in a mixed metal oxide nanoparticle; increasing the effective concentration of dopant species in a bacterial synthesis process and decreasing the effective toxicity of the dopant to the bacteria; and, providing a method for bacterial synthesis of reduced metal oxides using prealloyed precursor compounds. Further and other objects of the present invention will become apparent from the description contained herein.

SUMMARY OF THE INVENTION

In accordance with one aspect of the present invention, the foregoing and other objects are achieved by a method for producing mixed metal oxide compounds that includes the steps of: providing a supply of a metal reducing bacteria; providing a culture medium suitable for growth of the bacteria; providing a first mixed metal oxide phase comprising at least a first and a second metal, at least one of the first and second metal being reducible from a higher to a lower oxidation state by the bacteria; and, combining the bacteria, the culture medium, the first mixed metal oxide, and at least one electron donor in a reactor, wherein the bacteria reduces at least one of the first metal and the second metal from the higher to the lower oxidation state to form a second mixed metal oxide phase.

In accordance with another aspect of the present invention, a method for producing mixed metal oxide compounds includes the steps of: providing a supply of a thermophilic, metal reducing bacteria; providing a culture medium suitable for growth of the bacteria; providing a first mixed metal oxide phase comprising at least a first and a second metal, at least one of the first and second metal being reducible from a higher to a lower oxidation state by the bacteria; and, combining the bacteria, the culture medium, the first mixed metal oxide, and at least one electron donor in a reactor, wherein, at a temperature in the range of about 25° C. to about 85° C., the bacteria reduces at least one of the first metal and the second metal from the higher to the lower oxidation state to form a second mixed metal oxide phase.

For a better understanding of the present invention, together with other and further objects, advantages and capabilities thereof, reference is made to the following disclosure and appended claims in connection with the above-described drawings.

DETAILED DESCRIPTION OF THE INVENTION

The respiration process in thermophilic bacteria that results in Fe(III) reduction generally involves a hydrogen electron donor and an Fe(III) acceptor. The hydrogen is split, yielding two hydrogen ions and two electrons. The two electrons pass through one or more metabolic processes within the bacterial cell, providing energy for the bacterium. The specific metabolic pathways have not been identified. Ultimately, two electrons are donated by the bacterial cell to a suitable electron acceptor such as Fe(III), reducing it to Fe(II).

Figure 1:
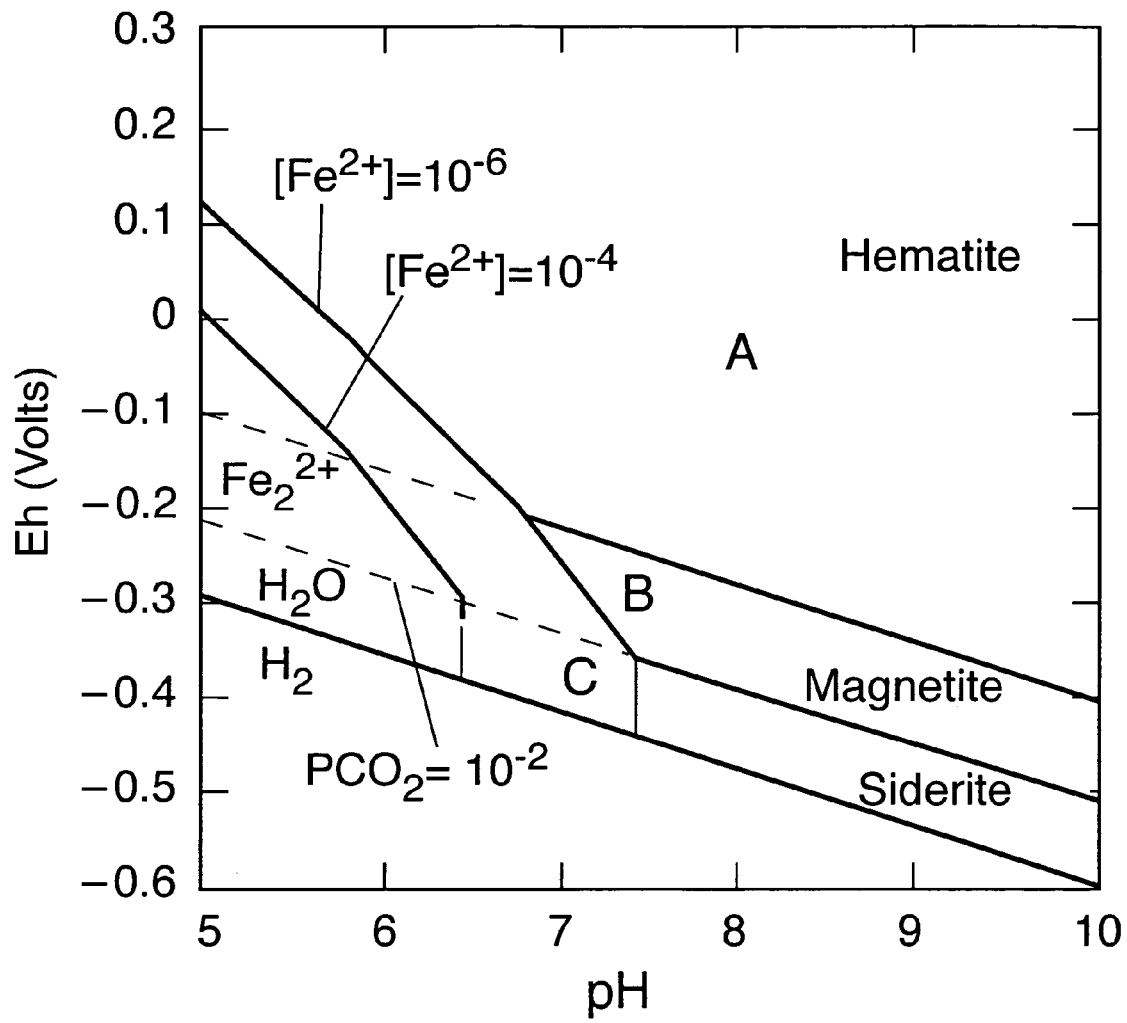
FIG. 1 is a is a redox potential-pH diagram illustrating regions of stability of various Fe-containing species and the electrochemical conditions established by thermophilic bacteria to facilitate the formation of magnetite.

Although the exact detailed steps of the mechanism by which thermophilic bacteria reduce ions are not known with certainty, the observed results may be placed into a thermodynamic context by considering the regions of stability of the various iron-containing species in a pH-potential plot (Pourbaix diagram) as shown in FIG. 1. For purposes of illustration, the discussion below focuses on the reduction of Fe(III); however, the concepts may be applied to other metal species.

Starting with an aqueous solution at pH of 8 and zero potential (Point A), any iron present will have a valence of +3, and a suspension of hydrous Fe(III) oxides will be stable. When thermophilic bacteria are added and provided with an electron donor source such as hydrogen, the hydrous Fe(III) oxides are converted to magnetite. The magnetite product phase comprises generally equiaxed euhedral crystals (typically cubes, octahedra, and modifications thereof as are typical of spinel-type oxides). One can see from the formula $Fe_3O_4$ (which may alternately be expressed as $FeO \cdot Fe_2O_3$) that in the magnetite formed, ⅔ of the Fe ions are still Fe(III). Thus, it is theorized that the bacteria are not simply "reducing Fe(III) to Fe(II)" until it is consumed, but are instead effectively moving the electrochemical potential of the system into the region where magnetite is the stable phase (Point B in FIG. 1). When all of the Fe(III) oxyhydroxide has been converted to magnetite, bacterial respiration ceases because the electrochemical potential of magnetite is such that it is not a usable electron acceptor in the bacterial system.

If one starts with a source of aqueous ferric ions such as FeO(OH) and adds an electron donor such as hydrogen (for example, by bubbling gaseous hydrogen through the solution) the equilibrium potential of the system initially lowers to some point generally indicated at Point C in FIG. 1. However, this only implies that the following reaction is thermodynamically favored.

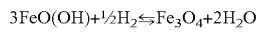

$$3FeO(OH) + \tfrac{1}{2}H_2 \leftrightarrows Fe_3O_4 + 2H_2O$$

Kinetic limitations effectively prevent a significant amount of product to be formed from this reaction at temperatures ranging from ambient to about 65° C.

When iron-reducing bacteria are added, the reaction proceeds to completion with substantially all FeO(OH) being converted to $Fe_3O_4$. Thus, in a sense, the bacteria may be considered a catalyst that facilitates the kinetics of the above reaction. In contrast to a chemical catalyst, the bacteria extract some metabolic energy to survive, so the equilibrium potential of the entire assemblage is slightly higher than it would be with the electron donor present but no bacteria, as indicated by the relative positions of Points B and C. Point B remains within the region where $Fe_3O_4$ is the stable phase, but now the reaction shown in Equation 1 is also kinetically favorable because of the crucial role played by bacterial respiration in splitting the hydrogen molecule and making electrons available at a suitable potential to reduce Fe(III) and form $Fe_3O_4$. Similar arguments may be applied to other electron donors such as lactate, pyruvate, formate, glucose, etc., for which overall reactions analogous to the one above can be written.

The reasoning discussed above was extended to the production of mixed metal oxides in which it has been further demonstrated that such mixed oxides can, under some circumstances, incorporate various metals that may or may not be reduced by the bacteria [see Lauf et al., U.S. Pat. No. 6,444,453]. The postulated mechanism was that the bacteria create an electrochemical environment that is favorable to the formation of a desired crystalline phase (say, a spinel-type ferrite) and as this phase forms it simply incorporates the soluble dopants as dictated by the overall crystal chemistry.

In earlier work synthesizing mixed oxides, Applicants observed that the concentrations of certain soluble dopants had to be limited to avoid toxicity to the bacteria. Specifically, 1.0 mM of $K_2CrO_4^{2-}$, 10 mM of $CoCl_2$ or Co(III)-EDTA, 2 mM of $NiCl_2$, and 1 mM of Cr(VI). The present invention provides a means to mitigate this problem by incorporating or prealloying the dopant species into the colloidal metal oxyhydroxide phase. Besides reducing the potential toxicity, the inventive method has the further benefit of enhancing the uniform, intimate mixing of the different metal species in the final product by providing an intimately mixed starting material. Furthermore, the invention may allow the incorporation of metal species whose low aqueous solubility would limit the amount of the species that could be carried as soluble ions in the culture medium. Additionally, if the several metal species are each reducible by the bacteria, the invention may help to produce a single-phase product and suppress the formation of two separate product phases.

Figure 2:
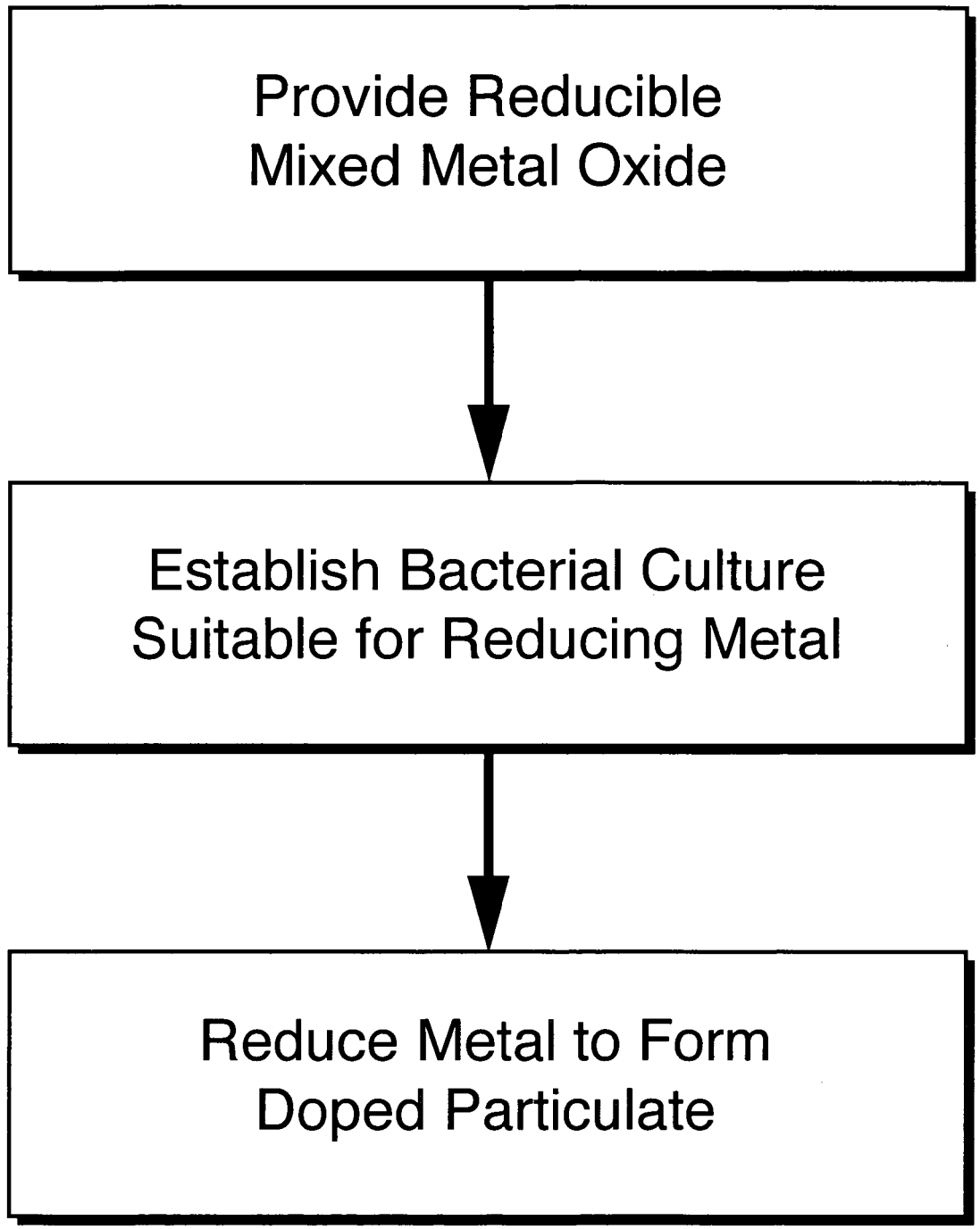
FIG. 2 is a process diagram illustrating a method for forming a mixed constituent crystalline phase in accordance with the present invention.

Referring to FIG. 2, a basic diagram for carrying out the present invention is provided. A mixed metal oxide is provided, preferably as a dispersed colloidal solid particulate, which is capable of being reduced from a higher to a lower oxidation state. Cultures are established using bacteria suitable for reducing the mixed metal oxide in the presence of an electron donor. The electron donor supports the respiration of the bacteria that culminates with reduction of the mixed metal oxide to a second, product phase. Any number of metal species may be incorporated in the mixed oxide, provided that, overall, the mixed oxide is capable of some reduction by the bacteria. Stated another way, the first mixed metal oxide must be a usable electron acceptor for the bacterial respiration process.

Applicants have demonstrated that the inventive process may be carried out with several known bacterial strains, and Applicants do not intend to limit the invention to any particular bacterial strain. In one embodiment, the preferred bacterial strain is *Thermoanaerobacter ethanolicus* strain TOR-39, a sample of which was deposited with the American Type Culture Collection (10801 University Blvd., Manassas, Va. 20010) on Sep. 7, 2001 as accession number PTA-3695. The conditions needed to grow and maintain this strain, including basal medium, nutrients, vitamins, and trace elements are enumerated in detail in U.S. Pat. No. 6,444,453. Strain TOR-39 is a thermophile that grows optimally at temperatures from about 65 to 85° C. Other thermophilic bacterial strains (defined herein as having optimal growth rates at temperatures generally greater than about 50° C.) are known that are capable of reducing various metals of interest: examples include thermophiles such as *T. ethanolicus* strain C1; *T. ethanolicus* strain M3; *Bacillus*

*infernus*; *Thermoterrabacterium ferrireducens* strain JW/AS-Y7; and *Thermus* sp. strain SA-01.

Metal reducing mesophilic or psychrotolerant bacteria (defined herein as having optimal growth rates at temperatures between about 10 and 40° C.) are also well known. Such bacteria are found in diverse environments, including deep marine sediments, sea ice, Antarctic lakes, and tundra permafrost. Exemplary bacteria include: *Shewanella alga*; *Shewanella gelidimarina*; *Shewanella frigidimarina*.

The choice of bacterial strain to use for a particular application will involve trade-offs relating to cost, efficiency, and properties. For example, thermophiles are often the preferred bacteria because a high temperature culture works faster and therefore produces more powder per unit of time. Conversely, subtle differences in the properties of the powders may be temperature related and in some cases more optimal properties might justify the lower growth rates characteristic of psychrophile cultures.

Pure FeO(OH) was traditionally prepared by neutralization (pH=7) of a 0.4 M $FeCl_3.6H_2O$ solution by slowly adding a 10 M NaOH solution with rapid stirring followed by washing and dispersion in deionized water to make the final amorphous iron oxyhydroxide suspension.

EXAMPLE I

Mixed-metal oxyhydroxide was prepared by slowly adding a 10 M NaOH solution into a mixture of 0.4 M $FeCl_3.6H_2O$ solution that contained another metal salt such as $MnCl_2.4H_2O$, $NiCl_2.6H_2O$, $CoCl_2.6H_2O$, $CrCl_3.6H_2O$, $ZnCl_2$, $NdCl_3.6H_2O$, $GdCl_3.6H_2O$, $HoCl_3.6H_2O$, $ErCl_3.6H_2O$, or $TbCl_2.6H_2O$. The NaOH was added with constant stirring until the pH reached 7. The resulting mixed oxide precipitates were washed five times with deionized water and then diluted to make a final doped Fe(III) oxyhydroxide suspension (0.4 M). These precursor compounds were flushed with nitrogen gas and stored under nitrogen but were not autoclaved before adding them to the bacterial culture. In each case, after adding the mixed oxide precursor compounds to the bacterial culture, ethanolicus Strain TOR-39 successfully reduced the mixed oxide precursor compounds and formed magnetic mixed oxide product compounds.

It is instructive to review here the postulated mechanism developed to explain the results of prior work, in which the bacteria were assumed to shed electrons into a substantially pure colloidal Fe(III) oxyhydroxide phase, and soluble dopant ions were then taken up into the growing product phase by one or more unidentified mechanisms. In that work, even though the end result was a mixed metal oxide, it could be attributed to a generally conventional operation of the bacterial respiration process. That is, it did not require the bacterium to do anything out of the ordinary in the electron transfer process, which presumably involves the operation of ferreductans or some similar specialized protein in the cell to transfer an electron specifically to an $Fe^{3+}$ ion.

By contrast, the results in the foregoing Example clearly show that the bacterium, surprisingly, was able to transfer an electron to a preexisting mixed metal oxide phase rather than simply to pure Fe(III) oxyhydroxide. It will be appreciated that this result has important implications for extending the process well beyond earlier limitations.

EXAMPLE II

Experiments were conducted using Fe with Co, Cr, and Ni dopants and as shown in Table I the method of the present invention allowed these dopants to be used at significantly higher concentrations than could be used when these metals were added to the culture as soluble salts. The increase is as much as a factor of five.

TABLE 1

Co, Cr, and Ni Concentrations in Doped Magnetites

| Metal | Old Method[a] | Present Invention |
|---|---|---|
| Cr | <1 mM | >1.8 mM |
|  | As 1.0 mM $K_2CrO_4^{2-}$ | As 36 mM $Cr_{0.05}Fe_{0.95}O(OH)$ |
| Co | <5 mM | >10.8 mM |
|  | As 10 mM Co(III)-EDTA | As 36 mM $Co_{0.3}Fe_{0.7}O(OH)$ |
| Ni | <2 mM | >10.8 mM |
|  | As 2 mM $NiCl_2$ | As 36 mM $Ni_{0.3}Fe_{0.7}O(OH)$ |

[a]Roh et al. "Microbial synthesis and the characterization of metal-substituted magnetites," Sol. St. Comm. 118, 529–34, 2001.

It is well known that many metals are toxic to microorganisms when present in aqueous solution. Different bacteria may display different sensitivities to various metal ions, but It must be emphasized that "toxicity" as used here may have a number of related manifestations. First, a soluble metallic species might be acutely toxic and kill the bacterial culture completely. Second, the metal might be tolerable at some concentration provided the precursor phase is introduced at a carefully measured rate and the product phase is removed at some corresponding rate. Third, the metal might simply slow the growth of the bacterial culture and adversely influence overall productivity. Thus, measures of toxic limits expressed in mM of bulk concentration in the culture medium are at best a simplification, but it is reasonable to suppose that all other things being equal a given metal will likely be tolerated better when it is in a relatively insoluble form than when it is in a completely soluble form.

The general cultural conditions for Fe-reducing psychrotrophic bacteria are well known in the art; [see, for example, Zhang et al., Iron reduction by psychrotrophic enrichment cultures, *FEMS Microbiology Ecology* 30, pp. 367–371 (1999), the entirety of which is incorporated herein by reference]. Such metal reducing bacteria may be employed when a lower-temperature synthesis process is desired.

EXAMPLE III

A psychrotolerant Fe(III)-reducing bacterium (*Shewanella alga* strain PV-1) which grows at temperatures from 0 to 37° C. was used in an attempt to synthesize Mn-doped magnetite. Runs were made using Mn mole fractions of 0.02, 0.05, 0.1, and 0.2 and the cultures were grown at room temperature. When a combination of "pure" Fe(III) oxyhydroxide (prepared as taught in U.S. Pat. No. 6,444,453) was added to the culture along with soluble $MnCl_2$, the bacteria did not form the desired magnetite phase. Surprisingly, when Mn—Fe oxyhydroxide was used instead, the bacteria successfully produced Mn-doped magnetite.

The foregoing example demonstrates several important aspects of the invention. First, the invention may be practiced using dissimilatory iron reducing bacteria that grow at ambient or lower temperatures and is not restricted to thermophilic cultures. Second, the inventive method facilitated the formation of the desired mixed oxide phase, which was not formed using prior teachings, and this benefit is completely independent of other stated benefits related to toxicity.

EXAMPLE IV

Various rare-earth substituted magnetites were prepared using the techniques described herein, and the compositions produced are given in the Table II. In the course of doing these tests, Applicants have discovered that for these compositions aging the mixed metal oxyhydroxide precursor at ambient temperature for at least several weeks and preferably for about a month greatly improved the yield of magnetite product formed.

TABLE II

Rare Earth-Substituted Magnetites

| Metal | Old Method (U.S. Pat. No. 6,444,453)[a] | Present Invention[b] |
|---|---|---|
| Nd | <0.2 mM of $NdCl_3 \cdot 6H_2O$ | >0.72 mM as $Nd_{0.02}Fe_{0.98}OOH$ |
| Gd | <0.2 mM of $GdCl_3 \cdot 6H_2O$ | >0.72 mM as $Gd_{0.02}Fe_{0.98}OOH$ |
| Er | <0.2 mM of $ErCl_3 \cdot 6H_2O$ | >0.72 mM as $Er_{0.02}Fe_{0.98}OOH$ |
| Ho | <0.2 mM of $HoCl_3 \cdot 6H_2O$ | >0.72 mM as $Ho_{0.02}Fe_{0.98}OOH$ |
| Tb | <0.2 mM of $TbCl_3 \cdot 6H_2O$ | >0.72 mM as $Tb_{0.02}Fe_{0.98}OOH$ |

[a]Note:
lanthanide concentrations of 0.2, 0.4, 0.8 and 2 mM were tested and no magnetite was formed in any case.
[b]Note:
lanthanide concentrations tested were 36 mM suspensions of lanthanide (Ln) doped mixed oxides: $Ln_{0.01}Fe_{0.99}OOH$, $Ln_{0.02}Fe_{0.98}OOH$, and $Ln_{0.05}Fe_{0.95}OOH$. Magnetite was formed in all cases except for the $Ln_{0.05}Fe_{0.95}OOH$ precursor.

The common feature of the foregoing examples is the combination of several metals into one solid precursor phase, which is dispersible in the culture medium on a very fine scale while avoiding the toxicity of soluble metal ions. A preferred means of doing this involves straightforward co-precipitation or sol-gel methods, which are well known in the art. Skilled artisans will, however, appreciate that many different routes exist to making various precursor materials that satisfy the basic characteristic that the precursor is a dispersible solid particulate phase that contains at least two different metal species. For example, colloidal Fe(III) oxyhydroxide may be treated in a solution of a second metal under conditions that allow the second metal to adsorb onto the surfaces of the Fe(III) oxyhydroxide particles. It will be understood that the surface adsorption step must be carried out such that the adsorbed species will not immediately desorb in solutions of the ionic strength typical of the bacterial culture being used. Alternatively, finely divided mixed metal oxide particles could be made by pyrolysis, chemical vapor decomposition, hydrolysis of metal alkoxides, or other means. The only requirement is that the mixed metal oxide precursor particles contain at least some metal ions that are reducible by the bacteria from a higher to a lower oxidation state, whereby bacterial respiration may proceed and the final product may be obtained.

For simplicity the foregoing discussion refers to a first metal and a second metal, but it will be understood that the inventive process is not limited to compositions of two metals but in fact can accommodate any desired number of metal species in a single batch.

Figure 3:
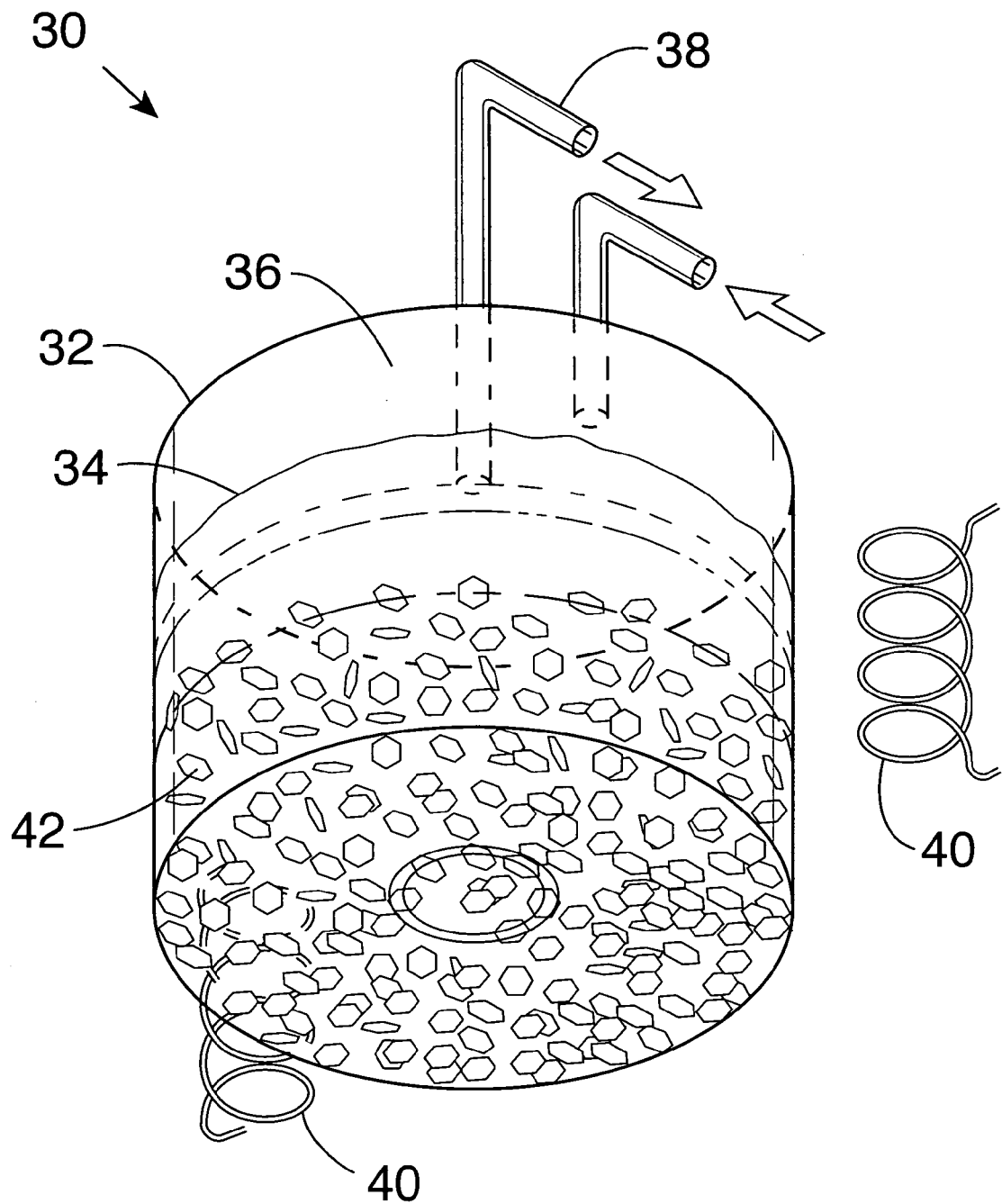
FIG. 3 illustrates a batch type reactor used to produce the mixed constituent crystalline phase.

FIG. 3 is a simplified diagram of a batch-type bioprocessing reactor 30 suitable for carrying out the inventive process shown in FIG. 2. The reactor includes a container 32 constructed of glass or other inert material. A culture medium 34 is introduced in the container 32. The culture medium 34 contains an aqueous solution of nutrients, trace elements, vitamins, and other organic and inorganic compounds as described in the foregoing examples. The solutions described above are provided for illustrative purposes. Other solution constructs are possible, depending on the specific implementation.

The container 32 is sealed to prevent the entry of air into the headspace gas region 36 thereby maintaining anaerobic conditions within the culture as well as permitting the inventive process to be carried out at pressures greater or less than ambient if desired. A gas conduit 38 is included to allow the introduction of selected gases into the container and to allow gases to exit the container. A heating element 40 is provided proximate the container 32 to maintain the culture medium 34 at a desired temperature for growth of the anaerobic, thermophilic bacteria. An electron donor is introduced into the culture either as a gas (such as hydrogen or CO) through the gas conduit 38, or dissolved directly into the culture medium 34 in the case of simple organics such as glucose, lactate, and pyruvate. An electron acceptor is provided in the form of one or more reducible transition elements, such as Fe(III), Cr(VI), Co(III), Ni(III), Mn(IV), and U(VI), etc. suspended in the culture medium 34. One or more additional dopant metal species, which may or may not be reducible, are incorporated in the suspended phase in the culture medium 34. If the dopant species is not reducible, for example Zn(II), it is generally present at a lower concentration than the reducible species. Exemplary dopant metals may include reducible or non-reducible metals, such as Fe(III), Cr(VI), Co(III), Ni(III), Mn(IV), U(VI), Ni(II), Al(III), Zn(II), Mg(II), Mn(II), Cu(II), Co(II), Pd(II), V(V), V(IV), V(III), Cu(II) Hg(II) Cd(II), Y(III), Nd(III), Gd(III), Ho(III), Er(III), or Tb(III).

In a particular embodiment, especially suitable for using *T. ethanolicus* strain TOR-39, the pH is maintained at a level between about 6.9 and 7.5, and the solution is maintained at a temperature of between about 45° C. and 75° C. Specific temperature and pH may be varied to optimize product yield, and the optimum values depend on factors including the particular mixed oxide being formed and the particular bacterial strain being used.

When hydrogen is used as the electron donor it may be introduced into the culture along with a relatively inert diluent or carrier gas such as $N_2$, Ar, He, $CO_2$, and the like. The gas mixture may preferably have a composition of at least 5% $H_2$ and more preferably around 80% $H_2$, with the balance comprising the carrier gas.

A crystalline product 42 forms in the container 32 as the bacteria reduce the reducible species. The dopant species, being already present in the solid precursor phase, is retained in the crystalline product 42, for example, $Fe_3O_4$, created through the reduction of the major metal species. When a sufficient quantity of crystalline product 42 has been produced and allowed to settle to the bottom of the container 32, the culture medium 34 is decanted and the crystalline product 42 is collected and washed. The incubation may be between 3 and 30 days, depending on the amount and size of the crystalline product desired.

Figure 4:
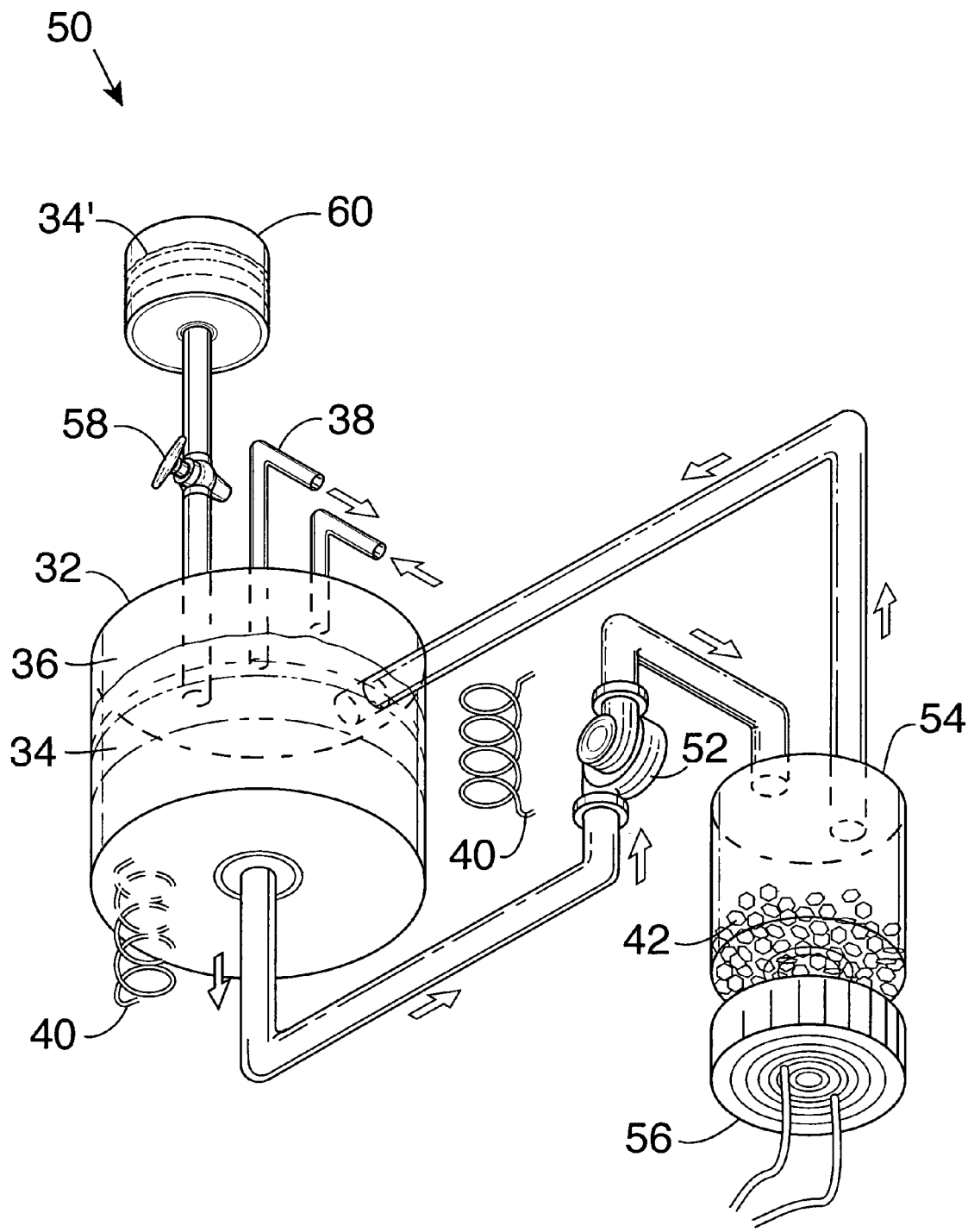
FIG. 4 illustrates a continuous type reactor used to produce the mixed constituent crystalline phase.

The disclosed process may also be performed in a continuous arrangement as shown schematically by the bioreactor 50 of FIG. 4. The bioreactor 50 operates in a similar manner as the bioreactor 30 of FIG. 3. The bioreactor 50 includes a fluid recirculator 52 that allows the culture medium 34 to pass through an external trap 54 from which the crystalline product 42 can be removed. The trap 54 may separate the crystalline product 42 from the circulating culture medium by settling, due to the greater density of the crystalline product 42. In many cases, the crystalline product 42 is magnetic, and the collection process can be assisted by using an electromagnet 56 or other suitable field-producing device to provide a magnetic field gradient in the trap 54.

Continuous collection of product from the circulating fluid may also be used as a means of controlling particle size, because the particles tend to grow larger the longer they remain in the culture. An additional fluid valve 58 may be provided through which additional culture medium or nutrients 34 may be added from an external reservoir 60 while maintaining the anaerobic conditions within the container 32.

EXAMPLE V

Pure magnetite was synthesized using the continuous reactor as shown schematically in FIG. 4. The culture was grown for a total of 8 days and product samples were extracted at 1, 2, 5, and 7 days. After 1 day the average particle size was about 8 nm; at 2 days the average size was about 9 nm; at 5 days the average particle size had increased to about 12 nm; at 7 days the particle size had grown to about 32 nm.

Obtaining and culturing specific metal reducing bacterial strains is considered to be a routine activity by those skilled in the art; various type culture collections in the U.S. and worldwide maintain repositories of available microorganisms and the general cultural requirements for specific strains are readily available in the scientific literature. For background purposes, typical cultural information is found in the following publications, the entireties of which are incorporated herein by reference.

The isolation, culture, and characterization of several psychrophilic bacteria are described in detail by: J. P. Bowman et al., "*Shewanella gelidimarina* sp. nov. and *Shewanella frigidimarina* sp. nov., Novel Antarctic Species with the Ability to Produce Eicosapentaenoic Acid (20:5ω3) and Grow Anaerobically by Dissimilatory Fe(III) Reduction," Int. J. of Systematic Bacteriology 47 [4], pp. 1040–47 (1997).

The isolation, culture and characterization of thermophilic bacteria are described in detail by: T. L. Kieft et al., "Dissimilatory Reduction of Fe(III) and Other Electron Acceptors by a *Thermus* Isolate," Appl. and Env. Microbiology, 65 [3], pp. 1214–21 (1999).

The isolation, culture, and characterization of mesophilic bacteria are described in detail by D. R. Lovley et al., "*Geobacter metallireducens* gen. nov. sp. nov., a microorganism capable of coupling the complete oxidation of organic compounds to the reduction of iron and other metals," Arch. Microbiol., 159, pp. 336–44 (1993).

Dissimilatory iron reducing bacteria are widely distributed and include some species in at least the following genera: *Bacillus, Deferribacter, Desulfuromonas, Desulfuromusa, Ferrimonas, Geobacter, Geospirillum, Geovibrio, Pelobacter, Sulfolobus, Thermoanaerobacter, Thermoanaerobium, Thermoterrabacterium,* and *Thermus*. Those skilled in the art will appreciate that the inventive method is general and may be usefully applied to cultures of any of these metal-reducing bacteria for particular applications of interest, including the synthesis of desired mixed metal oxide particulates. It will be further appreciated that the invention also provides a means of presenting the bacteria with specifically tailored electron acceptors, which could facilitate research intended to further elucidate bacterial respiration and metabolism.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A method of making a mixed metal oxide composition comprising the steps of:
   a. providing a supply of a metal reducing bacteria;
   b. providing a culture medium suitable for growth of said bacteria;
   c. providing a first mixed metal oxide phase comprising at least a first and a second metal, at least one of said first and second metal being reducible from a higher to a lower oxidation state by said bacteria; and,
   d. combining said bacteria, said culture medium, said first mixed metal oxide, and at least one electron donor in a reactor, wherein said bacteria reduces at least one of said first metal and said second metal from said higher to said lower oxidation state to form a second mixed metal oxide phase.

2. A method of making a mixed metal oxide composition in accordance with claim 1 wherein said first mixed metal oxide phase is a colloidal mixed oxide.

3. A method of making a mixed metal oxide composition in accordance with claim 1 wherein said electron donor is at least one selected from the group consisting of formate, glucose, lactate, acetate, pyruvate, and hydrogen.

4. A method of making a mixed metal oxide composition in accordance with claim 2 wherein hydrogen is provided to said reactor as a gaseous mixture comprising at least 5% $H_2$.

5. A method of making a mixed metal oxide composition in accordance with claim 1 wherein said first mixed metal oxide phase is prepared by the adsorption of at least one metal species onto the surface of a preexisting oxide of at least one other metal species.

6. A method of making a mixed metal oxide composition in accordance with claim 1 wherein said first mixed metal oxide phase contains at least two metals selected from the group consisting of Fe, Co, Cr, Cu, Ni, Mn, U, Al, Zn, Mg, V, Ag, Cd, Hg, Pd and rare earths.

7. A method of making a mixed metal oxide composition in accordance with claim 6 wherein said first mixed oxide phase contains Fe and at least one rare earth and said first mixed oxide phase is aged for at least two weeks in water before adding to the bacterial culture.

8. A method of making a mixed metal oxide composition in accordance with claim 1 wherein said bacteria comprise thermophilic bacteria of a genus selected from the group consisting of *Bacillus, Thermoanaerobacter, Thermoanaerobium, Thermoterrabacterium,* and *Thermus*.

9. A method of making a mixed metal oxide composition in accordance with claim 1 wherein said bacteria comprise mesophilic bacteria of a genus selected from the group consisting of *Shewanella, Geobacter, Geovibrio, Deferribacter, Ferromonas, Geospirillium,* and *Pelobacter*.

10. A method of making a mixed metal oxide composition in accordance with claim 1 wherein said first mixed metal oxide phase contains Fe and said second mixed metal oxide phase comprises a spinel-type ferrite.

11. A method of making a mixed metal oxide composition comprising the steps of:
   a. providing a supply of thermophilic, metal reducing bacteria;
   b. providing a culture medium suitable for growth of said bacteria;

c. providing a first mixed metal oxide phase comprising at least a first and a second metal, at least one of said first and second metal being reducible from a higher to a lower oxidation state by said bacteria; and, d. combining said bacteria, said culture medium, said first mixed metal oxide, and at least one electron donor in a reactor, wherein, at a temperature in the range of about 25° C. to about 85° C. said bacteria reduces at least one of said first metal and said second metal from said higher to said lower oxidation state to form a second mixed metal oxide phase.

12. A method of making a mixed metal oxide composition in accordance with claim 11 wherein said first mixed metal oxide phase is a colloidal mixed oxide.

13. A method of making a mixed metal oxide composition in accordance with claim 11 wherein said electron donor is at least one selected from the group consisting of formate, glucose, lactate, acetate, pyruvate, and hydrogen.

14. A method of making a mixed metal oxide composition in accordance with claim 12 wherein hydrogen is provided to said reactor as a gaseous mixture comprising at least 5% $H_2$.

15. A method of making a mixed metal oxide composition in accordance with claim 11 wherein said first mixed metal oxide phase is prepared by the adsorption of at least one metal species onto the surface of a preexisting oxide of at least one other metal species.

16. A method of making a mixed metal oxide composition in accordance with claim 11 wherein said first mixed metal oxide phase contains at least two metals selected from the group consisting of Fe, Co, Cr, Cu, Ni, Mn, U, Al, Zn, Mg, V, Ag, Cd, Hg, Pd, Y, and rare earths.

17. A method of making a mixed metal oxide composition in accordance with claim 11 wherein said thermophilic bacteria belong to a genus selected from the group consisting of *Bacillus, Thermoanaerobacter, Thermoanaerobium, Thermus*, and *Thermoterrabacterium.*

18. A method of making a mixed metal oxide composition in accordance with claim 11 wherein said first mixed metal oxide phase contains Fe and said second mixed metal oxide phase comprises a spinel-type ferrite.

* * * * *